(12) United States Patent
Fridman

(10) Patent No.: US 8,101,541 B2
(45) Date of Patent: Jan. 24, 2012

(54) CATALYST FOR DEHYDROGENATION OF HYDROCARBONS

(75) Inventor: Vladimir Fridman, Louisville, KY (US)

(73) Assignee: Sud-Chemie Inc., Louisville, KY (US)

(*) Notice: Subject to any disclaimer, the term of this patent is extended or adjusted under 35 U.S.C. 154(b) by 714 days.

(21) Appl. No.: 12/172,509

(22) Filed: Jul. 14, 2008

(65) Prior Publication Data

US 2010/0010280 A1  Jan. 14, 2010

(51) Int. Cl.
- *B01J 23/00* (2006.01)
- *B01J 23/02* (2006.01)
- *B01J 23/04* (2006.01)
- *B01J 23/06* (2006.01)

(52) U.S. Cl. ........ 502/317; 502/306; 502/308; 502/319; 502/320; 502/340; 502/341; 502/344

(58) Field of Classification Search .......... 502/306, 502/308, 317, 319, 320, 340, 341, 344
See application file for complete search history.

(56) References Cited

U.S. PATENT DOCUMENTS

| | | | |
|---|---|---|---|
| 2,374,404 | A | 4/1945 | Ahlberg |
| 2,375,402 | A | 5/1945 | Corson |
| 2,399,678 | A | 5/1946 | Houdry |
| 2,423,029 | A | 6/1947 | Houdry |
| 2,945,823 | A | 7/1960 | Cornelius |
| 2,956,030 | A | 10/1960 | Cornelius |
| 3,308,191 | A * | 3/1967 | Bajars ........................ 585/619 |
| 3,322,849 | A | 5/1967 | McEuen |
| 3,363,023 | A | 1/1968 | Mood |
| 3,488,402 | A | 1/1970 | Michaels |
| 3,719,721 | A | 3/1973 | Hansford |
| 3,801,672 | A | 4/1974 | Bajars |
| 3,846,340 | A | 11/1974 | Okuyama |
| 3,945,946 | A | 3/1976 | Hindin |
| 4,003,978 | A | 1/1977 | Shiraishi |
| 4,053,437 | A | 10/1977 | Liu |
| 4,181,602 | A | 1/1980 | Quick |
| 4,212,771 | A | 7/1980 | Hamner |
| 4,528,400 | A | 7/1985 | Cryberg |
| 4,677,237 | A | 6/1987 | Imai |
| 4,895,816 | A | 1/1990 | Gardner |
| 5,006,506 | A | 4/1991 | Hsieh |
| 5,141,912 | A | 8/1992 | Ernest |
| 5,258,567 | A | 11/1993 | Kerby |
| 5,284,811 | A | 2/1994 | Witt |
| 5,378,350 | A | 1/1995 | Zimmermann |
| 5,510,557 | A | 4/1996 | Gardside et al. |
| 5,846,507 | A | 12/1998 | Liu |
| 5,856,263 | A | 1/1999 | Bhasin |
| 6,096,679 | A | 8/2000 | Lonfils |
| 6,191,065 | B1 | 2/2001 | Williams et al. |
| 6,399,530 | B1 | 6/2002 | Chen |
| 6,417,422 | B1 | 7/2002 | Liu |
| 6,489,264 | B1 | 12/2002 | Isupova |
| 6,660,683 | B1 | 12/2003 | Yaluris |
| 6,989,346 | B2 | 1/2006 | Heineke et al. |
| 7,012,038 | B2 | 3/2006 | Alerasool |
| 7,294,604 | B2 * | 11/2007 | Dath et al. .................... 502/250 |
| 2005/0075243 | A1 * | 4/2005 | Fridman et al. ............... 502/306 |

FOREIGN PATENT DOCUMENTS

| | | |
|---|---|---|
| EP | 0947247 A1 | 10/1999 |
| GB | 1424382 | 2/1976 |
| WO | WO0168244 A2 | 9/2001 |
| WO | 2010/009076 A2 * | 1/2010 |

OTHER PUBLICATIONS

Rokicki, Andrzej, et al., Catalysts in Petroleum Refining and Petrochemicals, Proceeding of the Saudi-Japanese Symposium, 11th, Dhahran, Saudi Arabia, Nov. 11-12, 2001.

* cited by examiner

*Primary Examiner* — Patricia L Hailey
(74) *Attorney, Agent, or Firm* — Scott R. Cox

(57) ABSTRACT

A stationary or fluid bed dehydrogenation catalyst containing an alumina carrier, with chromium and alkali metals consisting of only sodium and potassium, added as promoters. The resultant catalyst demonstrates greater selectivity and olefin yield than prior art dehydrogenation catalysts, especially after aging.

18 Claims, No Drawings

CATALYST FOR DEHYDROGENATION OF HYDROCARBONS

BACKGROUND

The present invention relates to a catalyst for stationary and/or fluid bed dehydrogenation processes for hydrocarbons, which is particularly useful in vapor phase dehydrogenation to produce lower olefins. The catalyst preferably comprises an alumina carrier, with at least, chromium oxide, sodium oxide and potassium oxide. The resultant catalyst exhibits higher conversion and selectivity and high olefin yields after the catalyst ages, low deactivation rates and robust hydrothermal stability in comparison to prior art catalysts.

Supported metal oxide catalysts are used in a variety of commercial reactions, and are typically present in the form of pellets or other shaped products or powders having active metal sites on or within an essentially chemically inert carrier. In many catalytic processes, a chemical reactant contained in a gas stream is passed over or through a bed containing the catalyst. The reactant contacts the active site on the catalyst, a chemical conversion occurs to generate one or more products, and those products are released from the catalyst's active sites. For commercial operations, it is desirable that the gas stream be passed over the catalyst bed at an essentially constant and rapid rate.

In the production of olefins and diolefins by catalytic dehydrogenation, it is desirable to obtain as high a yield of the desired olefins or diolefins as possible with high conversion and selectivity during a single passage of the material to be catalyzed through the dehydrogenation zone. It is also important to produce as small an amount of by-products and coke during the dehydrogenation process as is possible. Further, long catalyst life and low deactivation rates are important.

Selectivity plays an important role in olefin production. As the annual production of olefins (such as isobutylene, propylene and butadiene) by catalytic dehydrogenation is at least 3 million tons, even relatively small increases in selectivity of the catalyst, as small as a fraction of a percentage point, can be very beneficial financially for olefin producers.

One of the most important of the dehydrogenation processes is the Houdry paraffin dehydrogenation process that is conducted in a cyclic reaction mode. Cyclic processes make use of parallel reactors that contain a shallow bed of the preferred catalyst. The feed is preheated through a fixed heater before passing over the catalyst in the reactors. The hot product is then cooled, compressed and sent to the product fractionation and recovery station. To facilitate continuous operation, the parallel reactors are operated in staggered, timed cycles. Each complete cycle typically consists of dehydrogenation, regeneration, reduction and purge segments. In addition, to provide more favorable equilibrium conditions, the reactors are generally operated at sub-atmospheric pressures during the dehydrogenation cycle. The regeneration cycle, operating in the range of 500 to 700° C., provides heat for the subsequent dehydrogenation reaction. Because of such high temperatures, the effective life of the dehydrogenation catalyst is generally no longer than about two to three years. After such periods of time on line, catalyst replacement is required because of reduced levels of conversion and selectivity. For instance, after two to three years of operation, the catalyst's conversion is generally reduced by 5 to 15% and its selectivity drops by about 5 to 20%. Thus, improvement in the catalyst's conversion and selectivity toward the end of a two to three year cycle can significantly improve the overall process efficiency.

While it is common to optimize a catalyst's performance based on its initial conversion and selectivity, it is also important to optimize catalyst performance based on its conversion and selectivity after aging.

Processes utilizing chromia-alumina catalysts for the conversion of paraffinic and olefinic hydrocarbons are well known and have been described in technical literature as well as in numerous patents starting in the 1940's. One typical composition for catalysts that are used for dehydrogenation of paraffins and olefins contains chromium oxide on the surface of an aluminum oxide carrier. Although chromia-alumina catalysts have a relatively high dehydrogenation activity, they often suffer from rapid coke formation during the dehydrogenation reaction. Consequently, frequent high temperature regeneration cycles are mandated. Because of these frequent regeneration cycles, it is required that the chromia-alumina catalyst have a high degree of hydrothermal stability in order to extend the life of the catalyst.

Other types of dehydrogenation catalysts contain platinum, palladium or other precious metals on various carriers, including alumina carriers. However, while both platinum-based and chromium-based dehydrogenation catalysts are used commercially, the nature and behavior of these two catalyst types are quite different.

For example, after regeneration, the small Pt particles on the surface of the platinum-based dehydrogenation catalysts become agglomerated, which causes a significant loss of activity. To return these catalysts to an active state, the Pt particles are subsequently re-dispersed by treatment with chloride. In contrast, chromium-based dehydrogenation catalysts require no such chloride treatment. In fact, chlorides are a severe poison for chromium-based dehydrogenation catalysts and must therefore be limited to no more than 1.0 ppmw in the form of HCl in the feed.

On the other hand, sulfur is a severe poison to platinum-based dehydrogenation catalysts, but chromium-based dehydrogenation catalysts can tolerate sulfur levels as high as 100 ppmw with little or no impact on performance.

These two types of dehydrogenation catalysts are also quite different from a compositional standpoint. In the case of platinum-based dehydrogenation catalysts, the active dehydrogenation component (Pt) is typically present in an amount of less than 1 wt %. In addition, these platinum-based catalysts require an element from Group IV as a promoter. They also typically contain a significant amount of a halogen (up to 1 wt %). In contrast, chromium-based dehydrogenation catalysts contain the active dehydrogenation component ($Cr_2O_3$) at higher percentage levels, typically 10-30 wt %, require no group IV element, and must not contain any halogen, as it is a poison.

These two types of dehydrogenation catalysts are also quite different from an operational standpoint. Platinum-based dehydrogenation catalysts require the hydrocarbon feed to be diluted with hydrogen and/or steam while chromium-based dehydrogenation catalysts require no hydrogen dilution with the feed and water is a poison for the catalyst.

Accordingly, a person skilled in the art would not anticipate that a change in composition of a platinum-based dehydrogenation catalyst which resulted in improved performance would necessarily cause a similar improvement in performance for a chromium-based dehydrogenation catalyst.

Additional components are often added to dehydrogenation catalysts to enhance their reactivity or selectivity or to enhance the operating characteristics of the carrier. One common additive is a single alkali metal or alkaline earth metal. Numerous patents have described the addition of an alkali metal to dehydrogenation catalysts, wherein the alkali metal of choice generally includes any of the alkali metals from lithium to cesium. Sodium or potassium compounds are often chosen for use because of their low cost and simplicity of utilization. It has generally been assumed that there is no significant difference in performance of the catalysts regardless of the choice of the alkali metal promoter although some references have recommended one alkali metal over other alkali metals.

There have also been some disclosures of a combination of alkali metals being utilized for chromium-based dehydrogenation catalysts. For example, U.S. Pat. No. 7,012,038 discloses a dehydrogenation catalyst which requires the addition of both lithium oxide and sodium oxide to a chromium oxide/alumina catalyst.

In addition, the use of lithium and potassium to a platinum-alumina dehydrogenation catalyst is disclosed in U.S. Pat. No. 4,677,237.

Notwithstanding the prior art, additional improved chromia/alumina catalysts with enhanced conversion and selectivity, especially as the catalyst ages, are still needed.

It is one object of the invention to produce a useful dehydrogenation catalyst comprising chromia distributed on an alumina carrier, which is promoted with both sodium oxide and potassium oxide. The use of sodium oxide and potassium oxide together as promoters provides enhanced performance for this inventive catalyst over prior art dehydrogenation catalysts, although this phenomenon primarily occurs after aging, wherein improvements in conversion and selectivity are particularly noted.

It is a further object of the invention to disclose useful processes for the preparation of the improved dehydrogenation catalysts comprising chromia deposited on a alumina carrier, which is promoted with both sodium oxide and potassium oxide.

It is a further object of the invention to disclose an improved process for dehydrogenating hydrocarbons, particularly lower paraffins, especially after the aging of the catalyst, wherein an improved dehydrogenation catalyst is utilized comprising chromia deposited on an alumina carrier, which is promoted with both sodium oxide and potassium oxide.

These and other objects of the invention can be obtained by the catalysts, the processes for preparation of the catalysts and the processes for dehydrogenation of hydrocarbons, particularly lower paraffins, which are disclosed herein.

SUMMARY OF THE INVENTION

The present invention discloses a stationary or fluid bed dehydrogenation catalyst comprising at least a carrier, chromium oxide, sodium oxide and potassium oxide. The present invention also discloses processes for preparation of a dehydrogenation catalyst wherein a carrier is prepared and then spray-dried or pelletized, dried, calcined and impregnated with a $CrO_3$ solution which includes sodium and potassium promoters. The present invention also discloses an alternative process for preparation of a dehydrogenation catalyst comprising mixing alumina with potassium, sodium and chromium compounds and calcining the end product. The resultant dehydrogenation catalyst demonstrates higher selectivity and conversion, primarily after aging, than prior art catalysts. The present invention further comprises a process for dehydrogenation of a dehydrogenatable hydrocarbon by contacting that hydrocarbon with a dehydrogenation catalyst comprising at least chromium oxide, sodium oxide and potassium oxide with an alumina carrier which shows improved performance over prior art catalysts, especially after aging.

DETAILED DESCRIPTION OF A PREFERRED EMBODIMENT

The catalyst of the present invention is intended for use in a stationary and/or fluid bed dehydrogenation process for converting dehydrogenatable hydrocarbons, preferably for converting $C_2$-$C_6$ hydrocarbons, to olefins and/or diolefins. Dehydrogenation reactions are normally conducted at the highest practical throughput rates which produce an optimum yield. Yield is dependent upon conversion and selectivity of the catalyst. These characteristics determine the efficiency of the process. Selectivity of the catalyst is defined as the ratio of the number of moles of the desired product, e.g. propylene, isobutylene or higher molecular weight olefin produced, to the number of moles of paraffin converted. Activity or conversion refers to that portion of feedstock that is converted to both the desired products and by-products. For high efficiency of the process, it is important to have both a high initial yield with the fresh catalyst and high activity and selectivity of the catalyst as the catalyst ages. For purposes of this disclosure, a catalyst is considered "aged" after it has been utilized for about 7-8 months on stream. Alternatively, a catalyst is considered "aged" after it has been "artificially aged" in the manner discussed later. Both of these criteria (initial yield and yield after aging) are used to determine the catalyst's overall efficiency.

The dehydrogenation catalyst of the present invention can be utilized in either a fluid bed or a stationary bed reactor.

As is known in the art, a supported metal oxide catalyst generally has one or more active metal oxides dispersed on, or compounded with, a carrier or support to act as a promoter or promoters. Among other features the support provides a means for increasing the surface area of the catalyst. Recommended carriers for the dehydrogenation catalyst of the invention include aluminum oxide, aluminas, such as gamma, beta, and theta alumina and the like or mixtures thereof, alumina monohydrate, aluminum trihydroxide, such as bayerite, nordstrandite, or gibbsite, or mixtures thereof, alumina-silica, transition aluminas, silica, silicates, zeolites and combinations thereof. Preferably, the carrier is formed from gamma, beta or theta alumina and the like. The carrier can be formed as a powder or in various shapes including, but not limited to, rings, spheres, cylinders, pellets, tablets, stars, tri-lobes, extrudates and the like. Commercial carriers of these types are well known in the industry.

For one type of dehydrogenation catalyst, chromium compounds are commonly used as the active phase because of its efficiency in paraffin dehydrogenation reactions. To persons skilled in the art, chromium-based dehydrogenation catalysts are not considered comparable to platinum and/or palladium-based dehydrogenation catalysts for the reasons previously discussed. Thus, in a preferred embodiment the catalyst of the invention do not contain platinum and/or palladium.

Typically, in dehydrogenation catalysts of this invention, the chromium compound is in the form of $Cr_2O_3$. The chromium may be derived from $CrO_3$ or inorganic chromium salts, such as ammonium chromate or dichromate or chromium nitrate or other chromium salts or mixtures thereof. The chromium compound is converted to chromium oxide during one or more heating processes. The catalyst of the present invention preferably comprises from about 10 wt % to about 30 wt % chromium in the form of $Cr_2O_3$, based on the total catalyst weight, including the $Cr_2O_3$. In a more preferred embodiment, the catalyst comprises from about 15 wt % to about 28 wt % chromium, and in a most preferred embodiment, the amount of chromium is from about 17 wt % to about 24 wt %, by weight.

The introduction of the chromium compound into or on the support material can take place by any process well known in the art. Nonexclusive examples include, but are not limited to, simultaneous precipitation of aluminum oxide and chromium oxide from an aqueous solution containing aluminum and chromium salts, simultaneous impregnation on the carrier, treating an alumina support with a solution of chromic acid and mixing chromium oxide with aluminum hydroxide or oxide.

It has been surprisingly determined that the performance of a chromia/alumina catalyst can be significantly improved by the addition of the combination of sodium oxide with potassium oxide. In addition, it has surprisingly been discovered that the particular ratios that are chosen between the sodium oxide and potassium oxide enhance the performance of the catalyst.

It has also been surprisingly discovered that a chromia/alumina dehydrogenation catalyst containing a combination of both sodium oxide and potassium oxide substantially outperforms, especially after aging, chromia/alumina catalysts containing either, but not both of, sodium oxide and potassium oxide and also chromia/alumina catalysts that contain different combinations of alkali metals. Specifically, it has been surprisingly discovered that the performance of a chromia/alumina dehydrogenation catalyst to which have been added both sodium oxide and potassium oxide outperforms, especially after aging, a chromia/alumina catalyst which contains sodium oxide and lithium oxide, as taught by U.S. Pat. No. 7,012,038. Thus, in a preferred embodiment, the preferred alkali metal oxides added to the chromia/alumina dehydrogenation catalyst consist of only sodium oxide and potassium oxide. Further, it has been surprisingly discovered that chromia/alumina dehydrogenation catalysts containing only sodium oxide and potassium oxide perform better than catalysts of a similar composition to which have been added additional alkali metals oxides, such as lithium oxide, especially after aging. Thus, in a most preferred composition the only alkali metal oxides added to the chromium-based dehydrogenation catalyst are sodium oxide and potassium oxide.

The preferred quantity of sodium oxide in the catalyst of the invention is from about 0.1 to about 2 wt. %, more preferably from 0.1 to 1 wt. %, based on the total weight of the catalyst, including the $Na_2O$, and most preferably from 0.1 to 0.3 wt %.

The preferred quantity of the potassium oxide is from 0.1 to about 5 wt. %, more preferably from about 0.1 to 2 wt. %, based on the total weight of the catalyst including the potassium oxide.

In a preferred embodiment the weight ratio of the potassium oxide to sodium oxide in the catalyst is from 0.1:1 to about 10:1, based on the total weight of the catalyst, and more preferably the weight ratio of the potassium oxide to sodium oxide is from 0.1:1 to 3:1.

If the catalyst is for use in a fluid bed, the catalyst preferably has a particle size of from about 20 μm to about 150 μm. The carrier may be prepared by a variety of techniques that are known in the art. Preferably, the carrier is spray-dried or pelletized and calcined at a temperature from about 500° C. to about 1100° C.

Dehydrogenation catalysts containing chromia sometimes contain one or more additional promoters other than alkali metal oxides that are added to improve selected properties of the catalyst or to modify the catalyst activity and/or selectivity. In the present invention, zirconium is preferably added to the catalyst as an additional promoter. The zirconium cation may be present in a variety of forms and from different zirconium sources, such as, $ZrO_2$, zirconium hydroxide, a zirconium basic carbonate or a similar zirconium-containing compound or mixtures thereof. The zirconium compound, calculated as $ZrO_2$, preferably comprises from about 0.1 wt % to about 15 wt %, based on the total catalyst weight, including the $ZrO_2$. In a more preferred embodiment, the catalyst comprises from about 0.1 wt % to about 5 wt % zirconium compound; and in a most preferred embodiment, the amount of the zirconium compound, is from about 0.5 wt % to about 1.5 wt %. The zirconium compound, may be added to the catalyst in a variety of methods, as are known in the art. In a preferred embodiment the zirconium, is co-impregnated with the chromium.

Magnesium may also be added to this catalyst as an additional promoter. The magnesium compound, calculated as magnesium oxide, comprises from about 0.1 to about 15 weight percent, based on the total catalyst weight, including the magnesium oxide. In a more preferred embodiment, the catalyst comprises from about 0.1 to about 2 weight percent magnesium compound, and in a most preferred embodiment the amount of magnesium compound, is from about 0.5 to about 1 weight percent. The magnesium compound, may be added to the catalyst in a variety of methods, as are known in the art. In a preferred embodiment the magnesium is co-impregnated with chromium.

In a preferred process for production of the catalyst, alumina pellets are prepared from aluminum trihydroxide, such as bayerite, gibbsite, nordstrandite or mixtures thereof, preferably bayerite, or other such alumina hydrates and aqueous nitric acid. The calcined alumina carrier is preferably in the form of gamma-, theta-, or beta-alumina and the like or mixtures thereof. In one embodiment the ingredients are admixed for a mixing time providing completion of the reaction of the nitric acid with the alumina. The mixture is then formed into an intermediate precursor in an appropriate form and shaped, as required. For example, the mixture may be extruded through die plates to form strands that are cut into pellets. Alternatively, the alumina can be formed into other shapes including, but not limited to spheres, tablets, cylinders, stars, trilobes and the like.

The obtained pellets, if used, are then dried and heat treated at appropriate temperatures for a period sufficient to develop an attrition resistant structure with a surface area from about 15 to about 350 $m^2/g$. These pellets, with or without adjustment of their surface area, are then impregnated, preferably with a solution of chromic acid with dissolved sodium and potassium compounds and, if desired, zirconium compounds, such as zirconium carbonate, and magnesium compounds, such as magnesium oxide. These additional components are added under conditions that produce a good distribution of the promoters on the carrier. The impregnated pellets are then dried at a temperature from about 90° C. to about 180° C. and calcined at a temperature from about 500° C. to about 1100° C. followed by a conditioning treatment in steam and air to fix the structure and initial activity of the catalyst.

In an alternative embodiment the dehydrogenation catalyst may be prepared by mixing the preferred alumina and the potassium, sodium and chromium compounds and other promoters, if desired, to form the end product followed by heat treatment at a temperature from about 500 to about 1,100° C., which is then followed by additional treatments as needed to fix the structure and activity of the catalyst.

The catalysts of the present invention are effective as dehydrogenation catalysts and are especially effective in promoting the dehydrogenation of propane, isobutane, n-butane and iso-pentane to produce the related olefins or diolefins. Thermodynamically beneficial conditions for this paraffin dehydrogenation reaction are 400-700° C., preferably 540-640° C., and at lower than atmospheric pressure, preferably 0.2-0.5 atmosphere. The contact time of the reactant-containing gas with the catalyst is expressed in terms of liquid-hourly-space velocity (LHSV), which is defined as the volume of liquid hydrocarbon reactant per volume of catalyst per hour. The LHSV of the reactant can vary between 0.1 hour$^{-1}$ and about 5 hour$^1$.

To predict catalyst stability over time, any suitable method can be used to age the catalyst, as is known in the art. Examples are long term tests in a small-scale adiabatic reactor at typical commercial operating conditions or placement of samples in baskets which are then loaded in a commercial reactor. Alternatively, a method of accelerating catalyst aging has been developed which is disclosed in "A New Houdry Catalyst for the 'Third Wave' Propane Dehydrogenation", M. A. Urbancic, V. Fridman, A. Rokicki North American Catalysis Society Meeting, Philadelphia, 2005, Paper O-266.

To evaluate the stability of the catalysts, besides performance tests, the physical-chemical properties of the aged catalysts, such as alpha-$(Cr,Al)_2O_3$ phase content, and surface area are determined. As a reduction of surface area and the appearance of alpha-$(Cr,Al)_2O_3$ in catalysts occur as a result of aging, they can be used as indirect indicators of catalyst stability. Thus, lower alpha-$(Cr,Al)_2O_3$ content and/or higher surface area in the aged catalysts indicates higher stability of the catalysts.

EXAMPLES

The following examples illustrate and explain the present invention, but are not to be taken as limiting the present invention in any regard. Parts and percentages are by weight unless otherwise designated.

Comparative Example 1

A dehydrogenation catalyst, with a composition of 19.7 wt. % $Cr_2O_3$ and 0.65 wt. % $Na_2O$ with the remaining part comprising alumina is prepared as follows:

Hard alumina pellets are prepared from aluminum trihydroxide and aqueous nitric acid. The ingredients are thoroughly admixed; the mixing time provides time for completion of the reaction of nitric acid with the alumina. The mixture is then formed into pellets of ⅛", diameter. The pellets are dried. The carrier is heat treated at 371° C. in an atmosphere of air and then heat-treated at 616° C. in air.

The aluminum oxide pellets are then impregnated with a solution of 42% by weight chromic acid and 1.1% sodium oxide to produce the weight percentages for the components listed above. The impregnated aluminum oxide is dried ten hours at 121° C. and calcined at 760° C. in 20 mol percent steam.

Inventive Example 2

The catalyst of Inventive Example 2 is prepared from the hard alumina pellets according to the process of Comparative Example 1. The hard alumina pellets are impregnated with a 42% by wt. solution of chromic acid, 0.4% by wt. sodium oxide and 1.1% by wt. potassium oxide to produce the weight percentages for the components that are listed below. The impregnated alumina pellets are dried ten hours at 121° C. and calcined at 760° C. according to the process of Comparative Example 1. The final formulation of the catalyst is 19.7 wt. % $Cr_2O_3$, 0.21 wt. % $Na_2O$, 0.52 wt. % $K_2O$, with the remaining portion being $Al_2O_3$.

Comparative Example 3

The catalyst of Comparative Example 3 is prepared from hard alumina pellets according to the process of Comparative Example 1. The hard alumina pellets are impregnated with a 42% by wt. solution of chromic acid and 1.8% by wt. potassium oxide to produce the weight percentages for the components that are listed below. The impregnated alumina pellets are dried several hours at 121° C. and calcined at 760° C. according to Comparative Example 1. The final composition of the catalyst is 19.7 wt. % $Cr_2O_3$ and 0.93 wt. % $K_2O$, with the remaining portion being $Al_2O_3$.

Comparative Example 4

The catalyst of Comparative Example 4 is prepared from hard alumina pellets according to the process of Comparative Example 1. The hard alumina pellets are impregnated with a solution of a mixture of a 42% by wt. solution of chromic acid, 0.95% by wt. sodium oxide, and 0.55% by wt. lithium oxide to produce the weight percentages for the components listed below. The impregnated alumina pellets are dried at 121° C. and calcined at 760° C. according to the process of Comparative Example 1. The final formulation of the catalyst is 19.5 wt. % $Cr_2O_3$, 0.5 wt % $Na_2O$, 0.3 wt % $Li_2O$, with the remaining portion being $Al_2O_3$.

Comparative Example 5

The catalyst of Comparative Example 5 is prepared from hard alumina pellets according to the process of Comparative Example 1. The hard alumina pellets are impregnated with a solution of a mixture of a 42% by wt. solution of chromic acid, 0.75% by wt. sodium oxide, and 0.25% by wt. lithium oxide, and 0.44% of potassium oxide to produce the weight percentages for the components listed below. The impregnated alumina pellets are dried at 121° C. and calcined at 760° C. according to the process of Comparative Example 1. The final formulation of the catalyst is 19.8 wt. % $Cr_2O_3$, 0.45 wt % $Na_2O$, 0.21 wt % $K_2O$, 0.11 wt % $Li_2O$, with the remaining portion being $Al_2O_3$.

The catalysts of Comparative Examples 1, 3, 4, 5 and Inventive Example 2 are artificially aged at the conditions described above. The fresh and aged samples are then evaluated for catalyst performance after aging to the equivalent of 7-8 months on stream in order to determine their stabilities.

Tests for isobutane dehydrogenation performance are conducted in an externally heated tubular reactor of 1" internal diameter. Isobutane is introduced to the catalysts at controlled throughput and pressure (LHSV=1.0 and pressure=0.33 atm.) over a range of temperatures. Dehydrogenation products are analyzed to determine conversion of isobutane and isobutene selectivity. To test the performance of the catalysts "after aging", the catalysts were artificially aged using the procedures disclosed in "A New Houdry Catalyst for the Third Wave", disclosed above.

Table 1 shows the effect of the addition of both potassium oxide and sodium oxide as promoters on the performance of the catalysts according to the invention.

TABLE 1

Composition and performance of the catalysts, fresh and after aging

| Example | $Cr_2O_3$ % [wt] | $Na_2O$ % [wt] | $K_2O$ % [wt] | $Li_2O$ % [wt] | Fresh Catalysts Performance at 1000° F. | | Aged Catalysts Performance | |
|---|---|---|---|---|---|---|---|---|
| | | | | | Isobutane conversion at 1000° F. | Isobutylene Selectivity | Isobutane conversion at 1050° F. | Isobutylene Selectivity at 60% conversion |
| Comparative Example 1 | 19.7 | 0.65 | 0 | 0 | 55.3 | 91.7 | 30.5 | 79.6 |
| Inventive Example 2 | 19.7 | 0.21 | 0.5 | 0 | 55.6 | 91.5 | 48.1 | 87.6 |
| Comparative Example 3 | 19.7 | 0 | 0.9 | 0 | 55.8 | 91.9 | 46.7 | 79.6 |
| Comparative Example 4 | 19.5 | 0.5 | 0 | 0.3 | 55.9 | 92.1 | 42.6 | 80.2 |
| Comparative Example 5 | 19.8 | 0.45 | 0.2 | 0.11 | 56.1 | 91.7 | 23.6 | 81.4 |

As shown in Table 1, after aging both the conversion and selectivity of the catalyst of Inventive Example 2 showed enhanced isobutane conversion and isobutylene selectivity over the catalysts of the Comparative Examples. This was a surprising result as the quantity of alkali metals present in Inventive Example 2 was similar to or less than the quantity of the alkali metals present in each of the Comparative Examples. Further, the performance of the Inventive Example 2 catalyst was especially surprising in comparison to the performance of Comparative Example 4, which used the composition disclosed in U.S. Pat. No. 7,012,038. Interestingly, the performance of the catalyst was not enhanced, and was in fact reduced when $Li_2O$ was additionally added to a catalyst already containing $Na_2O$ and $K_2O$. This was an especially surprising result.

The catalysts of the present invention are intended for use in stationary and/or fluid bed dehydrogenation processes. The composition of the catalysts and the processing condition may be varied without exceeding the scope of the invention.

The invention claimed is:

1. A catalyst for use in dehydrogenation processes comprising:
   a carrier; chromium oxide, at a concentration from about 10 wt % to about 30 wt % chromium oxide, based on the total catalyst weight, including the chromium oxide; sodium oxide, as a promoter, at a concentration from about 0.1 wt % to about 2 wt % sodium oxide based on the total catalyst weight, including the sodium oxide, and potassium oxide, as a promoter, at a concentration from about 0.1 wt % to about 5 wt % potassium oxide, based on the total catalyst weight, including the potassium oxide.

2. The catalyst of claim 1 wherein the carrier is selected from a group consisting of aluminum oxide, alumina, alumina monohydrate, aluminum trihydroxide, transition alumina, gamma-alumina, theta-alumina, eta-alumina, alumina-silica, silica, silicates, zeolites, bayerite, gibbsite, nordstrandite and combinations thereof.

3. The catalyst of claim 1 wherein the carrier has a particle size of from about 20 μm to about 150 μm.

4. The catalyst of claim 1 wherein the chromium oxide is present at a concentration from about 15 wt % to about 28 wt %, based on the total catalyst weight, including the chromium oxide.

5. The catalyst of claim 1 wherein the chromium oxide is added in the form of a $CrO_3$ solution that is impregnated onto the alumina carrier.

6. The catalyst of claim 1 wherein the potassium and sodium oxide promoters are co-impregnated on the carrier with the chromium.

7. The catalyst of claim 1 wherein the sodium oxide is present at a concentration of from about 0.1 wt % to about 1 wt % sodium oxide, based on the total catalyst weight, including the sodium oxide.

8. The catalyst of claim 1 wherein the sodium oxide is present at a concentration of about 0.1 wt % to about 0.3 wt % sodium oxide, based on the total catalyst weight, including the sodium oxide.

9. The catalyst of claim 1 wherein the potassium oxide promoter is present at a concentration of from about 0.1 wt % to about 2 wt % potassium oxide, based on the total catalyst weight, including the potassium oxide.

10. The catalyst of claim 1 wherein the ratio of potassium oxide to sodium oxide is from about 0.1:1 to about 10:1 on a weight basis.

11. The catalyst of claim 1 wherein the ratio of potassium oxide to sodium oxide is from about 0.1:1 to about 3:1 on a weight basis.

12. The catalyst of claim 1 further comprising at least one additional promoter selected from the group consisting of zirconium and magnesium compounds and mixtures thereof.

13. A catalyst for use in dehydrogenation processes comprising:
   a carrier; chromium oxide, at a concentration from about 10 wt % to about 30 wt % chromium oxide, based on the total catalyst weight, including the chromium oxide; sodium oxide, as a promoter, at a concentration from about 0.1 wt % to about 2 wt % sodium oxide based on the total catalyst weight, including the sodium oxide; potassium oxide, as a promoter, at a concentration from about 0.1 wt % to about 5 wt % potassium oxide, based on the total catalyst weight, including the potassium oxide; and from about 0.1 to about 15 wt % of zirconium oxide, based on the total catalyst weight.

14. A catalyst for use in dehydrogenation processes comprising:
   a carrier; chromium oxide, at a concentration from about 10 wt % to about 30 wt % chromium oxide, based on the total catalyst weight, including the chromium oxide; sodium oxide, as a promoter, at a concentration from about 0.1 wt % to about 2 wt % sodium oxide based on the total catalyst weight, including the sodium oxide; potassium oxide, as a promoter, at a concentration from about 0.1 wt % to about 5 wt % potassium oxide, based on the total catalyst weight, including the potassium oxide; and from about 0.1 to about 15 wt % of zirconium oxide, based on the total catalyst weight, and from about 0.1 to about 15 wt % of magnesium oxide, based on the total catalyst weight.

15. A catalyst for use in dehydrogenation processes comprising:
a carrier; chromium oxide, at a concentration from about 10 wt % to about 30 wt % chromium oxide, based on the total catalyst weight, including the chromium oxide; and alkali metal oxides consisting essentially of sodium oxide and potassium oxide as promoters, wherein the sodium oxide concentration is from about 0.1 wt % to about 2 wt %, based on the total catalyst weight and the potassium oxide concentration is from about 0.1 wt % to about 5 wt % based on the total catalyst weight.

16. A catalyst for use in dehydrogenation processes comprising:
a carrier; chromium oxide, at a concentration from about 10 wt % to about 30 wt % chromium oxide, based on the total catalyst weight, including the chromium oxide; alkali metal oxides consisting essentially of sodium oxide and potassium oxide as promoters, wherein the sodium oxide concentration is from about 0.1 wt % to about 2 wt %, based on the total catalyst weight, and the potassium oxide concentration is from about 0.1 wt % to about 5 wt % based on the total catalyst weight and zirconium oxide, as a promoter, at a concentration from about 0.1 to 15 wt % zirconium oxide, based on the total catalyst weight, including the zirconium oxide.

17. A process for making a dehydrogenation catalyst comprising
mixing and shaping an alumina compound to form a shaped carrier,
combining the shaped carrier with compounds comprising a chromium compound and alkali metal compounds, consisting essentially of a sodium compound and a potassium compound, to form a precursor material, and
heating the precursor material to form the dehydrogenation catalyst.

18. A process for making a dehydrogenation catalyst comprising
mixing alumina with compounds comprising chromium compounds and alkali metal compounds, consisting essentially of sodium and potassium compounds, to form a precursor material, and
heat treating the precursor material to form the dehydrogenation catalyst.

\* \* \* \* \*